United States Patent
Cushing et al.

(10) Patent No.: US 9,689,027 B2
(45) Date of Patent: Jun. 27, 2017

(54) HIGH EFFICIENCY MULTIPLEXED NUCLEIC ACID CAPTURE IN A STRUCTURED MICROENVIRONMENT

(71) Applicant: The Board of Trustees of the Leland Stanford Junior University, Palo Alto, CA (US)

(72) Inventors: Anna McGinty Cushing, New York, NY (US); Billy Tsz Cheong Lau, Palo Alto, CA (US); Hanlee P. Ji, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 149 days.

(21) Appl. No.: 14/533,996

(22) Filed: Nov. 5, 2014

(65) Prior Publication Data
US 2015/0140553 A1    May 21, 2015

Related U.S. Application Data

(60) Provisional application No. 61/905,013, filed on Nov. 15, 2013.

(51) Int. Cl.
*C12Q 1/68* (2006.01)
*B01L 3/00* (2006.01)

(52) U.S. Cl.
CPC .......... *C12Q 1/6834* (2013.01); *B01L 3/5021* (2013.01)

(58) Field of Classification Search
None
See application file for complete search history.

(56) References Cited

U.S. PATENT DOCUMENTS

| 5,700,642 A | | 12/1997 | Monforte et al. | |
| 6,046,005 A | * | 4/2000 | Ju | C12Q 1/6869 435/6.12 |
| 6,153,379 A | * | 11/2000 | Caskey | C12Q 1/6874 435/6.11 |
| 6,913,884 B2 | * | 7/2005 | Stuelpnagel | C12Q 1/6837 435/6.12 |
| 2002/0042112 A1 | * | 4/2002 | Koster | B01J 19/0046 435/174 |
| 2007/0128624 A1 | * | 6/2007 | Gormley | C12Q 1/6855 435/6.12 |
| 2010/0167954 A1 | * | 7/2010 | Earnshaw | C12Q 1/6855 506/17 |
| 2010/0248991 A1 | | 9/2010 | Roesler | |

OTHER PUBLICATIONS

Ekstrom et al. High throughput sequencing reveals diversity of Human Papillomaviruses in cutaneous lesions, Int J Cancer. Dec. 2011; 129(11): 2643-2650.*
Russom et al. Single-nucleotide polymorphism analysis by allele-specific primer extension of fluorescently labeled nucleotides in a microfluidic flow-through device, Electrophoresis. Jan. 2003; 24(1-2): 158-161.*
Griffin, T.J. and Smith, L.M. Single-nucleotide polymorphism analysis by MALDI-TOF mass spectrometry, Trends Biotechnol. Feb. 2000; 18(2): 77-84.*
Shumaker et al. Human Mutation 1996; 7: 346-354.*
Dynabeads DNA Direct Universal "For the isolation of PCR-ready genomic DNA from small samples" (Jul. 2012).
Bentley et al., "Whole-genome re-sequencing" Science Direct (2006); 16:545-552.

* cited by examiner

*Primary Examiner* — Angela M Bertagna
(74) *Attorney, Agent, or Firm* — James S. Keddie; Bozicevic, Field & Francis LLP

(57) ABSTRACT

Provided herein is a method for sample analysis. In some embodiments, the method may involve: a) enzymatically attaching a reactive group to nucleic acid molecules in a sample; b) covalently reacting the reactive group with surface exposed reactive sites on a porous support, thereby covalently tethering the nucleic acid molecules to the porous support; c) performing a primer extension reaction using the tethered nucleic acid molecules as a template to produce primer extension products; and d) eluting the primer extension products from the porous support, while leaving the tethered nucleic acid molecules tethered to the porous support.

14 Claims, 2 Drawing Sheets

HIGH EFFICIENCY MULTIPLEXED NUCLEIC ACID CAPTURE IN A STRUCTURED MICROENVIRONMENT

GOVERNMENT RIGHTS

This invention was made with Government support under grant HG000205 awarded by the National Institutes of Health. The Government has certain rights in this invention.

BACKGROUND

Next-generation sequencing has emerged as a platform for the high-throughput analysis of nucleic acids and their associated genetic systems. The capture of such nucleic acids, such as DNA and RNA, is an essential sample processing step for next-generation sequencing. It allows for the precise targeting of rare molecular species and separates them from undesirable ones in a sample. However, the current process is slow; a typical hybridization capture reaction takes between 24 hours to one week and suffers from significant nonspecific off-target reactions.

SUMMARY

Provided herein is a method for sample analysis. In some embodiments, the method may involve: a) enzymatically attaching a reactive group to nucleic acid molecules in a sample; b) covalently reacting the reactive group with surface exposed reactive sites on a porous support, thereby covalently tethering the nucleic acid molecules to the porous support; c) performing a primer extension reaction using the tethered nucleic acid molecules as a template to produce primer extension products; and d) eluting the primer extension products from the porous support, while leaving the tethered nucleic acid molecules tethered to the porous support. The enzymatically attaching step may be done by ligating an oligonucleotide comprising the reactive group to the nucleic acid molecules of the sample, or by incorporating a modified nucleotide containing a reactive group using another enzyme such as a terminal transferase or polymerase, for example. The covalently reacting step may be done in a variety of different ways. In one embodiment, the covalently reacting step may be done using click chemistry. In these embodiments, the enzymatically attaching step may involve attaching an alkyne or azide group (which groups react together to form a covalent linkage in the presence of copper) to the nucleic acid molecules of the sample. This embodiment may be done by ligating an oligonucleotide containing an alkyne or azide group to the nucleic acid molecules of the sample.

The reactive sites on the porous support comprises a group that is specifically reactive with the reactive group added to the nucleic acid molecules. For example, if the nucleic acid molecules have an added alkyne group then the porous support may contain an azide group. Likewise, if the nucleic acid molecules have an added azide group then the porous support may contain an alkyne group.

In some embodiments, the porous support may be composed of a membrane, e.g., a silica membrane, or packed beads that are made of, for example, a sugar- or acrylamide-based polymer and having a diameter in the range of 1 μm to 250 μm, e.g., 50 μm to 150 μm. Other forms of silica, e.g., silica gels or beads could be used in certain cases.

In certain embodiments, the primer extension reaction may be done using gene specific primers that hybridize to a subset of the nucleic acid molecules that are tethered to the porous support. In these embodiments, the primers may hybridize to a sequence that is upstream from a region of interest (e.g., a site of a polymorphism or mutation) such that, when the primers are extended, a copy of the reverse complement of the region of interest is produced. In other embodiments, the primer extension reaction may be done using universal primers that hybridize to an oligonucleotide that is appended to the nucleic acid molecules. In these embodiments, all of the tethered nucleic acid molecules may be copied in the primer extension reaction. In certain embodiments, the primers may be barcoded so that one can identify from which support (and therefore which sample) the primer extension products were made, after the primer extension products are sequenced.

The sample may contain any type of nucleic acid, e.g., RNA (such as mRNA) or DNA. In some embodiments, the sample contains genomic DNA, e.g., genomic DNA that has been fragmented using physical treatment (e.g., sonication or shearing), enzymatic treatment (e.g., using a restriction enzyme), chemical treatment, or using a transposon/transposase-based method. In particular embodiments, the sample is obtained from a clinical sample, e.g., a tissue biopsy. In some cases, the nucleic acid molecules may be obtained from a formalin-fixed, paraffin embedded (FFPE) sample. In some cases, the sample may be obtained from a human patient having a condition or disease, e.g., cancer, an infectious disease, an inflammatory disease, or the like.

The eluting step of the method may be done using a variety of different methods. In some embodiments, the eluting step may be treating the product of step c) above with heat or a chaotrophic agent to denature the primer extension products from the tethered nucleic acid molecules, and then applying a force that separates the primer extension products and the porous support. The force may be a centrifugal force. In these embodiments, the porous support may be in the form of a spin column. In other cases, a magnetic force may be used. In these embodiments, the porous support may be attached to magnetic beads, allowing the beads to be separated from the eluted primer extension products using a magnetic field.

The eluted primer extension products may be analyzed in a variety of different ways. For example, the eluted primer extension products may be sequenced.

Because the primer extension products are eluted from the porous support without removing the tethered nucleic acid molecules from the matrix, the column may be re-used. In these embodiments the method may further comprise, after step d) above, performing a second primer extension reaction using the tethered nucleic acid molecules as a template to produce second primer extension products. The second primer extension products may be different from the initial primer extension products.

Also provided is a kit comprising a porous support that comprises surface-exposed reactive sites and an oligonucleotide comprising a reactive group, wherein the reactive sites and the reactive group are chosen such that they can specifically react with one another to produce a covalent linkage between the porous support and the oligonucleotide. As noted above, the porous support may be comprise surface exposed azide or alkyne groups. In some embodiments, the porous support may be in the form of a spin column, where the spin column comprises: a) a housing comprising an inlet and an outlet; b) within the housing, the porous support; and c) a first frit and a second frit, wherein the frits are porous and retain the porous support within the housing. In particular cases, the housing contains a lip that is dimensioned to fit over the wall of a microcentrifuge tube, thereby allowing the spin column to be placed inside a microcentrifuge tube and centrifuged.

BRIEF DESCRIPTION OF THE FIGURES

Certain aspects of the following detailed description are best understood when read in conjunction with the accompanying drawings. It is emphasized that, according to common practice, the various features of the drawings are not to scale. On the contrary, the dimensions of the various features are arbitrarily expanded or reduced for clarity. Included in the drawings are the following figures.

DEFINITIONS

Figure 1:
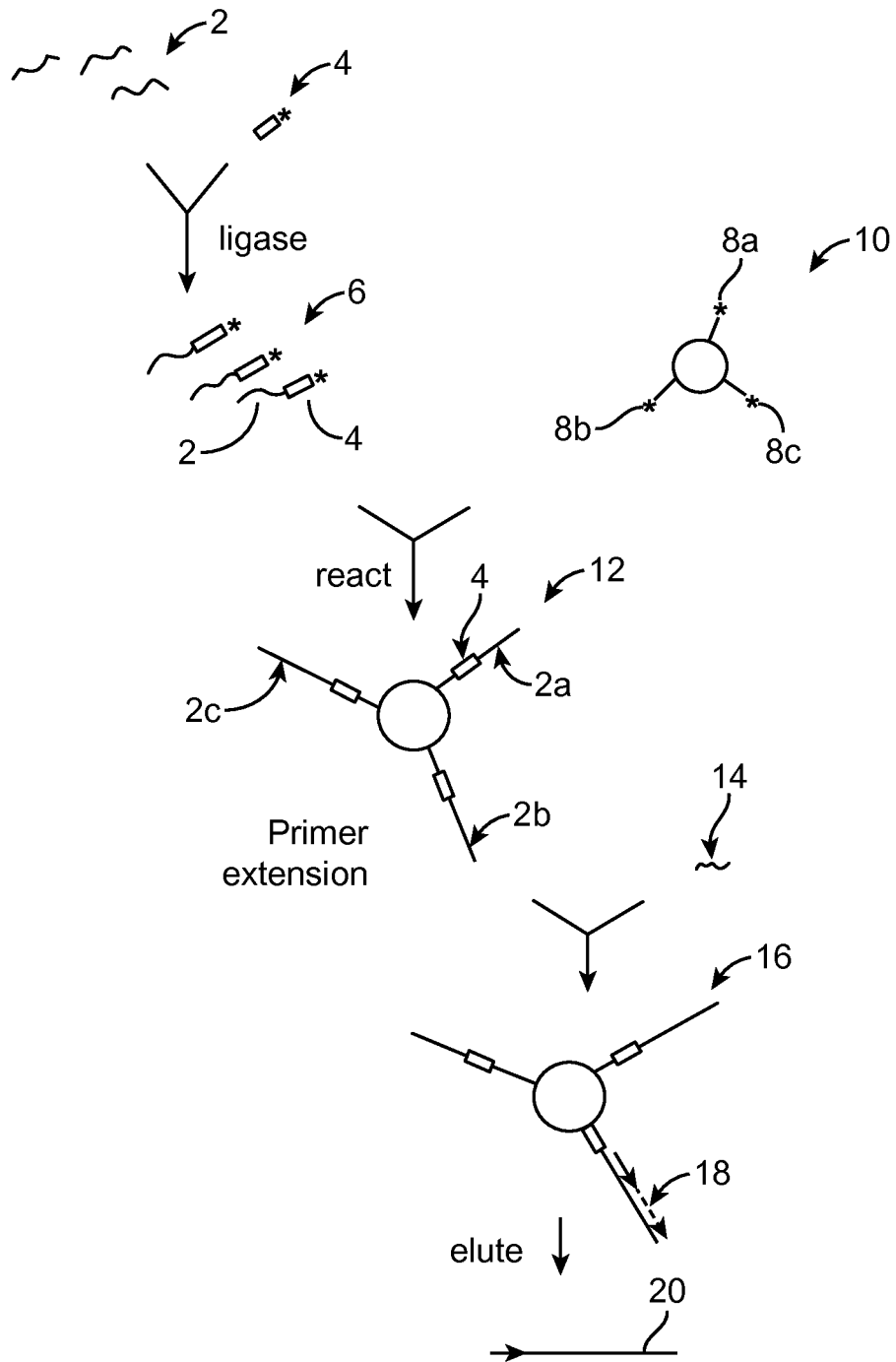
FIG. 1. schematically illustrates on implementation of the present method.

Unless defined otherwise herein, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

All patents and publications, including all sequences disclosed within such patents and publications, referred to herein are expressly incorporated by reference.

Numeric ranges are inclusive of the numbers defining the range. Unless otherwise indicated, nucleic acids are written left to right in 5' to 3' orientation; amino acid sequences are written left to right in amino to carboxy orientation, respectively.

The headings provided herein are not limitations of the various aspects or embodiments of the invention. Accordingly, the terms defined immediately below are more fully defined by reference to the specification as a whole.

Unless defined otherwise, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Markham, THE HARPER COLLINS DICTIONARY OF BIOLOGY, Harper Perennial, N.Y. (1991) provide one of skill with the general meaning of many of the terms used herein. Still, certain terms are defined below for the sake of clarity and ease of reference.

The term "sample" as used herein relates to a material or mixture of materials, typically, although not necessarily, in liquid form, containing one or more analytes of interest. The nucleic acid samples used herein may be complex in that they contain multiple different molecules that contain sequences. Fragmented genomic DNA and cDNA made from mRNA from a mammal (e.g., mouse or human) are types of complex samples. Complex samples may have more then $10^4$, $10^5$, $10^6$ or $10^7$ different nucleic acid molecules. A DNA target may originate from any source such as genomic DNA, cDNA (from RNA) or artificial DNA constructs. Any sample containing nucleic acid, e.g., genomic DNA made from tissue culture cells, a sample of tissue, or an FFPE samples, may be employed herein.

The term "nucleotide" is intended to include those moieties that contain not only the known purine and pyrimidine bases, but also other heterocyclic bases that have been modified. Such modifications include methylated purines or pyrimidines, acylated purines or pyrimidines, alkylated riboses or other heterocycles. In addition, the term "nucleotide" includes those moieties that contain hapten or fluorescent labels and may contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, are functionalized as ethers, amines, or the likes.

The term "nucleic acid" and "polynucleotide" are used interchangeably herein to describe a polymer of any length, e.g., greater than about 2 bases, greater than about 10 bases, greater than about 100 bases, greater than about 500 bases, greater than 1000 bases, up to about 10,000 or more bases composed of nucleotides, e.g., deoxyribonucleotides or ribonucleotides, and may be produced enzymatically or synthetically (e.g., PNA as described in U.S. Pat. No. 5,948,902 and the references cited therein) which can hybridize with naturally occurring nucleic acids in a sequence specific manner analogous to that of two naturally occurring nucleic acids, e.g., can participate in Watson-Crick base pairing interactions. Naturally-occurring nucleotides include guanine, cytosine, adenine and thymine (G, C, A and T, respectively).

The term "nucleic acid sample," as used herein denotes a sample containing nucleic acids.

The term "target polynucleotide," as use herein, refers to a polynucleotide of interest under study. In certain embodiments, a target polynucleotide contains one or more sequences that are of interest and under study.

The term "oligonucleotide" as used herein denotes a single-stranded multimer of nucleotide of from about 2 to 200 nucleotides, up to 500 nucleotides in length. Oligonucleotides may be synthetic or may be made enzymatically, and, in some embodiments, are 30 to 150 nucleotides in length. Oligonucleotides may contain ribonucleotide monomers (i.e., may be oligoribonucleotides) or deoxyribonucleotide monomers, for example. An oligonucleotide may be 10 to 20, 11 to 30, 31 to 40, 41 to 50, 51 to 60, 61 to 70, 71 to 80, 80 to 100, 100 to 150 or 150 to 200 nucleotides in length, for example.

The term "hybridization" refers to the process by which a strand of nucleic acid joins with a complementary strand through base pairing as known in the art. A nucleic acid is considered to be "selectively hybridizable" to a reference nucleic acid sequence if the two sequences specifically hybridize to one another under moderate to high stringency hybridization and wash conditions. Moderate and high stringency hybridization conditions are known (see, e.g., Ausubel, et al., Short Protocols in Molecular Biology, 3rd ed., Wiley & Sons 1995 and Sambrook et al., Molecular Cloning: A Laboratory Manual, Third Edition, 2001 Cold Spring Harbor, N.Y.). One example of high stringency conditions include hybridization at about 42 C in 50% formamide, 5×SSC, 5×Denhardt's solution, 0.5% SDS and 100 ug/ml denatured carrier DNA followed by washing two times in 2×SSC and 0.5% SDS at room temperature and two additional times in 0.1×SSC and 0.5% SDS at 42° C.

The term "duplex," or "duplexed," as used herein, describes two complementary polynucleotides that are base-paired, i.e., hybridized together.

The term "amplifying" as used herein refers to generating one or more copies of a target nucleic acid, using the target nucleic acid as a template.

The terms "determining", "measuring", "evaluating", "assessing," "assaying," and "analyzing" are used interchangeably herein to refer to any form of measurement, and include determining if an element is present or not. These terms include both quantitative and/or qualitative determinations. Assessing may be relative or absolute. "Assessing the presence of" includes determining the amount of something present, as well as determining whether it is present or absent.

The term "using" has its conventional meaning, and, as such, means employing, e.g., putting into service, a method or composition to attain an end. For example, if a program is used to create a file, a program is executed to make a file, the file usually being the output of the program. In another example, if a computer file is used, it is usually accessed, read, and the information stored in the file employed to attain an end. Similarly if a unique identifier, e.g., a barcode is used, the unique identifier is usually read to identify, for example, an object or file associated with the unique identifier.

As used herein, the term "$T_m$" refers to the melting temperature of an oligonucleotide duplex at which half of the duplexes remain hybridized and half of the duplexes dissociate into single strands. The $T_m$ of an oligonucleotide duplex may be experimentally determined or predicted using the following formula $T_m=81.5+16.6(\log_{10} [\text{Na}^+])+0.41$ (fraction G+C)−(60/N), where N is the chain length and [Na$^+$] is less than 1 M. See Sambrook and Russell (2001; Molecular Cloning: A Laboratory Manual, 3$^{rd}$ ed., Cold Spring Harbor Press, Cold Spring Harbor N.Y., ch. 10). Other formulas for predicting $T_m$ of oligonucleotide duplexes exist and one formula may be more or less appropriate for a given condition or set of conditions.

The term "denaturing," as used herein, refers to the separation of a nucleic acid duplex into two single strands.

The term "genomic sequence", as used herein, refers to a sequence that occurs in a genome. Because RNAs are transcribed from a genome, this term encompasses sequence that exist in the nuclear genome of an organism, as well as sequences that are present in a cDNA copy of an RNA (e.g., an mRNA) transcribed from such a genome.

The term "genomic fragment", as used herein, refers to a region of a genome, e.g., an animal or plant genome such as the genome of a human, monkey, rat, fish, insect or plant. A genomic fragment may or may not be adaptor ligated. An adaptor ligated genomic fragment may have an adaptor ligated to one or both ends of the fragment, or to at least the 5' or the 3' end of a molecule.

In certain cases, an oligonucleotide used in the method described herein may be designed using a reference genomic region, i.e., a genomic region of known nucleotide sequence, e.g., a chromosomal region whose sequence is deposited at NCBI's Genbank database or other database, for example. Such an oligonucleotide may be employed in an assay that uses a sample containing a test genome, where the test genome contains a binding site for the oligonucleotide.

The term "ligating", as used herein, refers to the enzymatically catalyzed joining of the terminal nucleotide at the 5' end of a first DNA molecule to the terminal nucleotide at the 3' end of a second DNA molecule.

The term "adaptor" refers to double stranded as well as single stranded molecules.

A "plurality" contains at least 2 members. In certain cases, a plurality may have at least 10, at least 100, at least 100, at least 10,000, at least 100,000, at least 10$^6$, at least 10$^7$, at least 10$^8$ or at least 10$^9$ or more members.

If two nucleic acids are "complementary", each base of one of the nucleic acids base pairs with corresponding nucleotides in the other nucleic acid. The term "complementary" and "perfectly complementary" are used synonymously herein.

A "primer binding site" refers to a site to which a primer hybridizes in an oligonucleotide or a complementary strand thereof.

The term "separating", as used herein, refers to physical separation of two elements (e.g., by size or affinity, etc.) as well as degradation of one element, leaving the other intact.

The term "sequencing", as used herein, refers to a method by which the identity of at least 10 consecutive nucleotides (e.g., the identity of at least 20, at least 50, at least 100 or at least 200 or more consecutive nucleotides) of a polynucleotide are obtained.

The term "adaptor-ligated", as used herein, refers to a nucleic acid that has been ligated to an adaptor. The adaptor can be ligated to a 5' end or a 3' end of a nucleic acid molecule.

The term "barcode sequence", as used herein, refers to a unique sequence of nucleotides used to identify and/or track the source of a polynucleotide in a reaction. A barcode sequence may be at the 5'-end or 3'-end of an oligonucleotide. Barcode sequences may vary widely in size and composition; the following references provide guidance for selecting sets of barcode sequences appropriate for particular embodiments: Brenner, U.S. Pat. No. 5,635,400; Brenner et al, Proc. Natl. Acad. Sci., 97: 1665-1670 (2000); Shoemaker et al, Nature Genetics, 14: 450-456 (1996); Morris et al, European patent publication 0799897A1; Wallace, U.S. Pat. No. 5,981,179; and the like. In particular embodiments, a barcode sequence may have a length in range of from 4 to 36 nucleotides, or from 6 to 30 nucleotides, or from 8 to 20 nucleotides.

The term "enzymatically attaching", as used herein, refers to the covalent addition of a reactive group onto a nucleic acid using an enzyme. Such an addition may be done using a ligase, terminal transferase, polymerase, or another enzyme that is capable of attaching an oligonucleotide or a nucleotide that contains the reactive group onto the nucleic acid. In attaching the reactive group, the reactive group is unmodified during the addition.

The term "covalently reacting", as used herein, refers to a chemical reaction in which new covalent bonds are formed between two different moieties.

The term "click chemistry", as used herein, refers to a specific chemistry for joining compounds, particularly biopolymers, together. Click chemistry includes [3+2] cycloadditions, such as the Huisgen 1,3-dipolar cycloaddition, e.g., the Cu(I)-catalyzed stepwise variant (see Spiteri et al. Angewandte Chemie International Edition 2010 49: 31-33, thiol-ene click reactions, the Diels-Alder reaction and inverse electron demand Diels-Alder reaction, [4+1] cycloadditions between isonitriles (isocyanides) and tetrazines, nucleophilic substitution especially to small strained rings like epoxy] and aziridine compounds, carbonyl-chemistry-like formation of ureas, and addition reactions to carbon-carbon double bonds like dihydroxylation or the alkynes in the thiol-yne reaction. One click chemistry of particular interest includes the azide alkyne Huisgen cycloaddition using a copper (or another metal such as ruthenium or silver) catalyst at room temperature. Click chemistry, including azide-alkyne cycloaddition, is reviewed in a variety of publications including Kolb et al (Angewandte Chemie International Edition 2001 40: 2004-2021), Evans (Australian Journal of Chemistry 2007 60: 384-395) and Tornoe (Journal of Organic Chemistry 2002 67: 3057-3064).

The terms "reactive group" and "reactive site" are used herein to distinguish between the two moieties that can react with one another to produce a covalent bond (e.g., in the click chemistry described above) between to elements. For the purposes of this disclosure, the "reactive group" is the group that is present on the nucleic acid whereas the "reactive site" is present on the porous support. However, it is understood that in some cases, the reactive group can be a first moiety (e.g., an alkyne) and the reactive site can be an a second moiety that specifically reacts with the first moiety (e.g., an azide) whereas in other cases the reactive group can be the second moiety (e.g., an azide) and the reactive site can be the first moiety (an alkyne). Notably, the reaction that occurs between a reactive group and a reactive site does not affect ability of the nucleic acid to base pair with other complementary sequences.

The term "porous support", as used herein, refers to a support that is porous. Porous supports are well known in the chromatography art and include membranes, packed beads, as well matrices that include cross-linked polymers. In some cases, a porous support may be made from a sugar- or acrylamide-based beads having a diameter of 10 μm to 500 μm (e.g., 25 μm to 250 μm) that are produced in solution (i.e., in hydrated form). Beads may be supplied as wet slurries that can be easily dispensed to fill and pack a column of any size. Such beads are extremely porous and sufficiently large to allow nucleic acid to flow as freely into and through the beads as they can between and around the surface of the beads. Other porous supports include membranes, e.g., silica membranes, and are commonly used to purify nucleic acids.

The term "covalently tethering", as used herein, refers to an action that results in a first element, e.g., a nucleic acid, being joined to a second element, e.g., a porous support, by a covalent bond. Covalently tethering may be direct or indirect (e.g., via another molecule, e.g., an oligonucleotide of another type of linker) that is covalently added either of the first element or the second element.

The term "free in solution," as used here, describes a molecule, such as a primer extension product, that is not bound or tethered to another molecule.

The term "primer extension reaction", as used herein, refers to the extension of a primer by the addition of nucleotides using a polymerase. If a primer that is annealed to a nucleic acid is extended, the nucleic acid acts as a template for extension reaction.

The term "primer extension products", as used herein, refers to the products of a primer extension reaction.

The term "eluting", as used herein, refers to the liquid phase separation of a product (e.g., a primer extension product) from a support. In most cases, the product that is eluted is collected, e.g., in a vessel.

The term "gene specific primer", as used herein, refers a primer that is designed to hybridize to a single target sequence in the genome of an organism under study. In certain cases, the target sequence may have been duplicated, in which case a gene specific primer may hybridize to multiple sequences, where each of the multiple sequences is a duplicate of another. In many cases, a gene specific primer may bind upstream of a sequence of interest, where a sequence of interest may have a role in a disease or condition, and may be polymorphic (e.g., may contain a potential mutation or SNP), and extension of the gene specific primer may produce a copy of the sequence of interest.

The term "universal primer", as used herein, refers to a primer that is designed to bind to all of the nucleic acid molecules in a sample.

The term "spin column", as used herein, refers to a chromatography column that is designed to a sample, wash and elution solvents (and optionally other liquids such as a reaction mix) can be added to the column and retained in the column until a centrifugal force (e.g., an RCF in the range of e.g., 50 to 15000, e.g., 50 to 500, depending on the type of support) is applied to the column. RCF may be estimated by the following formula RCF=$1.12\ r(rpm/1000)^2$, where r is the radius of the rotor used.

Other definitions of terms may appear throughout the specification.

DETAILED DESCRIPTION OF EXEMPLARY EMBODIMENTS

As noted above, in certain embodiments, the method may involve enzymatically attaching a reactive group to nucleic acid molecules in a sample, and then covalently reacting the added reactive group with reactive sites in a porous support to covalently tether the nucleic acid molecules to the porous support. A variety of different reactive groups and reactive sites may be used in the method. For example, bis-NHS esters and maleimides (which react with amines and thiols, respectively), may be used. In other cases, the reactive group and reactive sites may react with one another via click chemistry, as described above. In particular embodiments, nucleic acid molecules in the sample may be modified to contain an alkyne or azide group. Methods for making oligonucleotides that contain such groups are known (see, e.g., Ming et al Nucleic Acids Symp. Ser. 2008 52: 471-472; Seela et al Bioconjugate Chem., 2008 19: 211-224; Lietard et al Tetrahedron Letters, 2007, 48, 8795-8798; El-Sagheer et al Chembiochem 2008 9: 50-2, Chan et al Org. Lett. 2004 6: 2853-2855; WO2006117161, EP1877415, U.S. Pat. No. 8,129,315, WO2008952775 and WO03101972, which are incorporated by references) and oligonucleotides that contain such groups are available from a variety of retailers including Glen Research (Sterling, Va.).

As illustrated in FIG. 1, this initial step of the method may involve ligating an oligonucleotide 4 containing the reactive group (shown as an asterisk) to fragments of DNA 2. The product of this step is a population of nucleic acid molecules 6 that contain the reactive group. Each nucleic acid molecule 2 in this population contains an appended oligonucleotide 4 that contains a reactive group. The reactive group may be in the 3' end of the oligonucleotide, the 5' end of the oligonucleotide, or in the middle of the oligonucleotide, for example, and the oligonucleotide may be ligated to the nucleic acid molecules by its 5' end or its 3' end.

In certain cases, the fragments of DNA may be produced from genomic DNA using chemical, physical, restriction enzyme or transposase-catalyzed fragmentation methods, see, e.g., Adey et al (Genome Biology 2010, 11:R119). For example, the physical fragmentation methods may be sonication, nebulization, or shearing of genomic DNA. In certain embodiments, prior to performing the method, genomic DNA may be fragmented to an average size in the range of 100 bp to 10 kb, e.g., 200 bp to 5 kb. In certain embodiments, a subject reaction mix may further contain a nucleic acid sample. In particular embodiments, the sample may contain genomic DNA or an amplified version thereof (e.g., genomic DNA amplified by WGA using the Lage method (Lage et al, Genome Res. 2003 13: 294-307), "MDA" (Dean et al Proc. Natl. Acad. Sci. 2002 99: 5261-5266 and Nelson Biotechniques 2002 Suppl:44-47) or by multiple annealing and looping based amplification cycles ("MalBac"; see Zong et al Science. 2012 338: 1622-1626), for example. In exemplary embodiments, the genomic sample may contain genomic DNA from a mammalian cell, such as, a human, mouse, rat, or monkey cell. The sample may be made from cultured cells or cells of a clinical sample, e.g., a tissue biopsy, scrape or lavage or cells of a forensic sample (i.e., cells of a sample collected at a crime scene). In particular embodiments, the genomic sample may be from a formalin fixed paraffin embedded (FFPE) sample.

In particular embodiments, the nucleic acid sample may be obtained from a biological sample such as cells, tissues, bodily fluids, and stool. Bodily fluids of interest include but are not limited to, blood, serum, plasma, saliva, mucous, phlegm, cerebral spinal fluid, pleural fluid, tears, lacteal duct fluid, lymph, sputum, cerebrospinal fluid, synovial fluid, urine, amniotic fluid, and semen. In particular embodiments, a sample may be obtained from a subject, e.g., a human, and it may be processed prior to use in the subject assay. For example, the nucleic acid may be extracted from the sample prior to use, methods for which are known.

The next step of the method involves covalently reacting the reactive group with reactive sites in a porous support to covalently tether the nucleic acid molecules to the porous support. As illustrated in FIG. 1, this system involves contacting populations of nucleic acid molecules 6 with the porous support 10 that contains reactive sites 8a, 8b and 8c. As would be apparent, the porous support may be composed of beads, a membrane, or some other form of continuous matrix, where the porous support contains a large number of reactive sites. Further, the exact number of reactive sites on the surface of the porous support (which surface can be on the exterior or interior of the support) may vary greatly. The porous support may be made from any suitable material, including, but not limited to agarose, cellulose, dextran, polyacrylamide, latex, silica and controlled pore glass. The reactive sites on the porous support can be generated by using modifying agents such as functionalized silanes and active esters, methods for which are known. The reactive sites can also be generated by the addition of monomers containing reaction sites in a polymerization reaction that generates the porous matrix. The reactive groups in the nucleic acid molecules and reactive sites in a porous support are contacted under conditions suitable for those groups to react with one another to produce a covalent bond. If click chemistry is used, the groups may be contacted in the presence of copper or another suitable metal. Other reaction conditions are for other chemistries. Various silica membranes as well as methods for making the same are described in, e.g., US20120108418, US20120018370 and US20120009346, which are incorporated by reference for those methods.

The product 12 of this step is a porous support that comprises a plurality of nucleic acid molecules covalently tethered thereto. As illustrated, each of the tethered nucleic acid molecules contains the oligonucleotide 4, as well as a fragment of DNA 2. As illustrated, three different DNA molecules (2a, 2b and 2c) are bound to the porous support. In practice, a substantial portion (e.g., at least 50% of the molecules) of the population of nucleic acid molecules 6 (which may be as complex as an entire genome) may bind to the porous support.

The next step of the method involves performing a primer extension reaction using the tethered nucleic acid molecules as a template to produce primer extension products. This step is performed in column, such that the reaction is done while the nucleic acid molecules are still tethered to the support. As would be apparent, this step of the method involves hybridizing a primer 14 to the tethered nucleic acid, adding other necessary reagents, (e.g., polymerase, buffer and nucleotides), and then incubating the product 16 under conditions suitable for primer extension. Primer extension product 18 is produced by this reaction. In some embodiments, the primers used for primer extension may be gene specific in that they hybridize to a subset of the nucleic acid molecules that are tethered to the porous support. In some embodiments, the primer extension step may use a single gene specific primer to copy a single sequence (including any variants thereof) from the sample. In other embodiments, the primer extension step may use multiple gene specific primers to copy several sequences (including any variants thereof) from the sample. In other embodiments, a universal primer, i.e., a primer that is designed to hybridize to all tethered sequences may be employed. In some embodiments, this primer may hybridize to the oligonucleotide 4, whereas in other embodiments, this primer may hybridize to an adaptor that was ligated to the nucleic acid sample prior to ligation to the oligonucleotide 4. Depending on the desired result, the gene specific primers may be pathogen-specific primers (where each primer only primes in the genome of a particular pathogen) or locus-specific (where each primer only primes in the genome of the organism under study, e.g., the human genome). In any of these embodiments, the polymerase may proceed towards the support, or away from the support.

Next, the primer extension products are eluted from the porous support, while leaving the template tethered to the porous support, to produce an eluted primer extension product 20. This step may be done by treating the product of the primer extension step with heat (e.g., a temperature of at least 90° C.) or a chaotrophic agent (e.g., sodium iodide, sodium perchlorate, formamide, guanidinium thiocyanate or guanidinium hydrochloride) to denature the primer extension products from the tethered nucleic acid molecules; and applying a force that separates the primer extension products and the porous support. In one embodiment, the force may be a centrifugal force. However, other methods may be used.

After the primer extension product has been eluted from the support, a second primer extension reaction may be done using the same tethered nucleic acid molecules as a template to produce second primer extension products. The support—and the tethered nucleic acid molecules—may be reused several times.

In certain embodiments, the initial DNA being analyzed may be derived from a single source (e.g., a single organism, virus, tissue, cell, subject, etc.), whereas in other embodiments, the nucleic acid sample may be a pool of nucleic acids extracted from a plurality of sources (e.g., a pool of nucleic acids from a plurality of organisms, tissues, cells, subjects, etc.), where by "plurality" is meant two or more. As such, in certain embodiments, a nucleic acid sample can contain nucleic acids from 2 or more sources, 3 or more sources, 5 or more sources, 10 or more sources, 50 or more sources, 100 or more sources, 500 or more sources, 1000 or more sources, 5000 or more sources, up to and including about 10,000 or more sources. Molecular barcodes may allow the sequences from different sources to be distinguished after they are analyzed. In addition, the reaction may be multiplexed such that a plurality of different target loci (e.g., 10 to 1000) are targeted in a single reaction. In these embodiments, the samples may contain a molecular barcode in order to identify the source of a nucleic acid molecule after it is sequenced. In some cases, the barcode is contained within the oligonucleotide 4, which is linked to the nucleic acid molecules at the beginning of the method.

The eluted primer extension product may be analyzed by any suitable method. In one embodiment, the primer extension primer may contain a 5' tail that is compatible with use in a next generation sequencing platform, e.g., Illumina's reversible terminator method, Roche's pyrosequencing method (454), Life Technologies' sequencing by ligation (the SOLiD platform) or Life Technologies' Ion Torrent platform. Examples of such methods are described in the following references: Margulies et al (Nature 2005 437: 376-80); Ronaghi et al (Analytical Biochemistry 1996 242: 84-9); Shendure (Science 2005 309: 1728); Imelfort et al (Brief Bioinform. 2009 10:609-18); Fox et al (Methods Mol Biol. 2009; 553:79-108); Appleby et al (Methods Mol Biol. 2009; 513:19-39) and Morozova (Genomics. 2008 92:255-64), which are incorporated by reference for the general descriptions of the methods and the particular steps of the methods, including all starting products, reagents, and final products for each of the steps. In some cases, the primer may also contain a molecular barcode, positioned downstream of an amplification and/or sequencing primer binding sites, that can be used to identify from which sample a sequence is derived, or to count how many different starting molecules have been sequenced.

In other embodiments, the amplicon may be sequenced using nanopore sequencing (e.g. as described in Soni et al Clin Chem 53: 1996-2001 2007, or as described by Oxford Nanopore Technologies). Nanopore sequencing is a single-molecule sequencing technology whereby a single molecule of DNA is sequenced directly as it passes through a nanopore. A nanopore is a small hole, of the order of 1 nanometer in diameter. Immersion of a nanopore in a conducting fluid and application of a potential (voltage) across it results in a slight electrical current due to conduction of ions through the nanopore. The amount of current which flows is sensitive to the size and shape of the nanopore. As a DNA molecule passes through a nanopore, each nucleotide on the DNA molecule obstructs the nanopore to a different degree, changing the magnitude of the current through the nanopore in different degrees. Thus, this change in the current as the DNA molecule passes through the nanopore represents a reading of the DNA sequence. Nanopore sequencing technology as disclosed in U.S. Pat. Nos. 5,795,782, 6,015,714, 6,627,067, 7,238,485 and 7,258,838 and U.S. Pat Appln Nos. 2006003171 and 20090029477.

Kits

Figure 2:
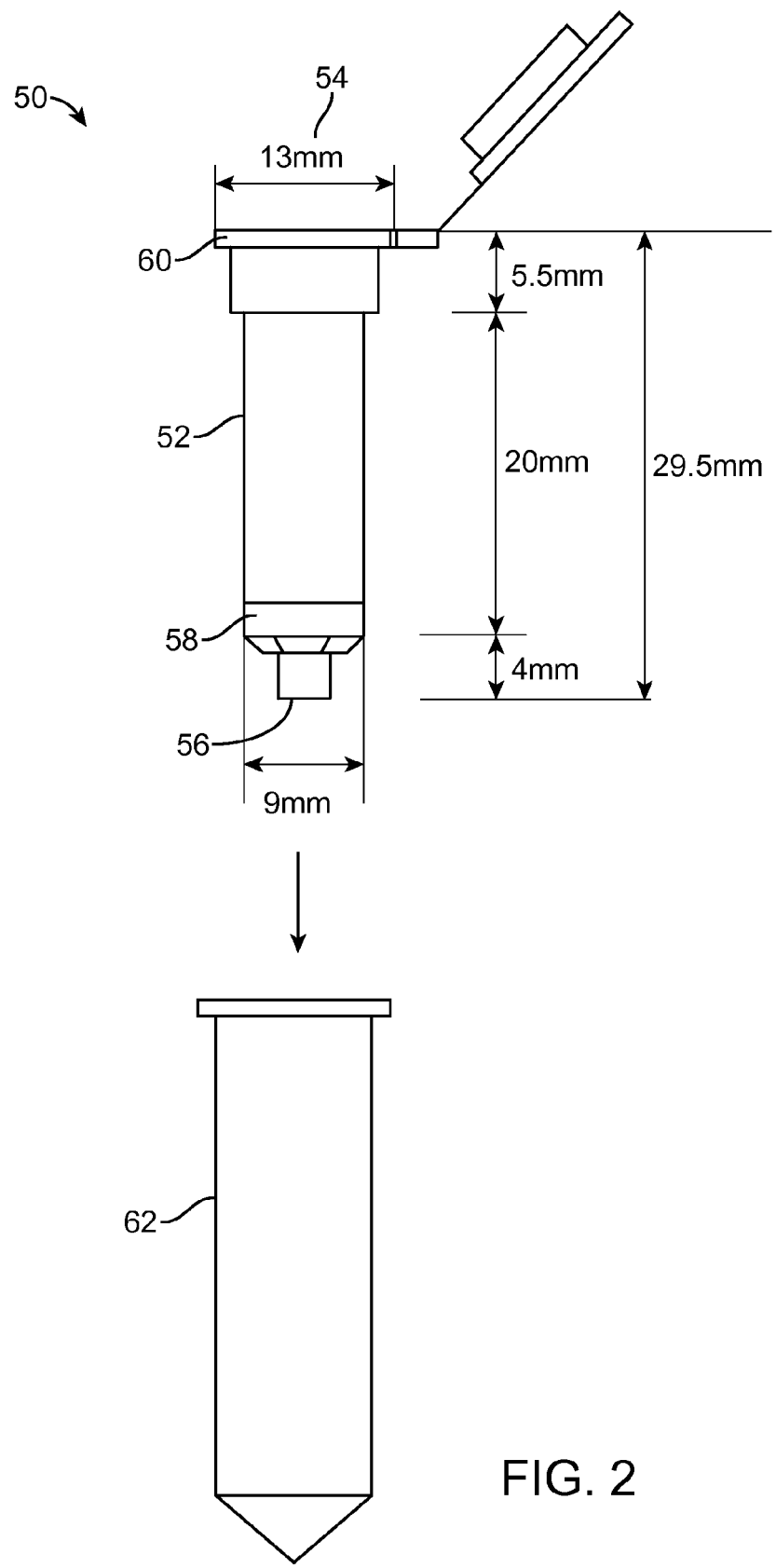
FIG. 2. schematically illustrates a spin column that can be used in the present method.

Also provided by the present disclosure are kits for practicing the subject method as described above. In certain embodiments, a subject kit may contain a kit comprising: a porous support that comprises surface-exposed reactive sites and an oligonucleotide comprising a reactive group, where the reactive sites and the reactive group are chosen such that they can specifically react with one another to produce a covalent linkage between the porous support and the oligonucleotide. As would be apparent from the above, the porous support may be composed of a membrane, e.g., a silica membrane, or beads and in some cases may contain surface exposed azide or alkyne groups. As illustrated in FIG. 2, in certain embodiments, the support may be contained in a spin column 50 that comprises a) a housing 52 comprising an inlet 54 and an outlet 56; and b) within the housing, the porous support 58. In certain cases the column may contain a first frit and a second frit, wherein the frits are porous and retain the porous support within the housing. The column may contain a lip 60 that is dimensioned to fit over the perimeter wall of a centrifuge (e.g., microcentrifuge) tube 62 that is used for collection of the product. The dimensions shown in FIG. 2 are exemplary. In practice, in certain embodiments, the length of the column may be anywhere from 10 mm to 10 cm (depending on the size of the tube). In certain embodiments, in certain the bed volume may be 50 µl to 1 ml, 100 µl to 400 µl. A standard microcentrifuge tube (1.5 ml or 2.0 ml) has an internal diameter of approximately 10 mm and an external diameter (at the lid) of approximately 12 mm. Thus, in certain embodiments, the present spin column may have outer width of 7 mm to 9.5 mm, and a lip of 1 mm to 2 mm, thereby allowing the spin column to be placed in a standard microcentrifuge tube without falling to the bottom of the tube.

The kit may also contain other reagents described above and below that may be employed in the method, e.g., adaptors, primers, ligase, hybridization buffers, etc.

In addition to above-mentioned components, the subject kit typically further includes instructions for using the components of the kit to practice the subject method. The instructions for practicing the subject method are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or sub-packaging) etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate. Other required components may include related computer programs and/or computer scripts to implement a modification to prior programs already installed on a sequencer. In addition to the instructions, the kits may also include one or more control analyte mixtures, e.g., two or more control analytes for use in testing the kit.

Utility

The method described above can be employed to manipulate and analyze DNA from virtually any nucleic acid source, including but not limited to genomic DNA and complementary DNA, plasmid DNA, mitochondrial DNA, synthetic DNA, and BAC clones etc. Furthermore, any organism, organic material or nucleic acid-containing substance can be used as a source of nucleic acids to be processed in accordance with the present invention including, but not limited to, plants, animals (e.g., reptiles, mammals, insects, worms, fish, etc.), tissue samples, bacteria, fungi (e.g., yeast), phage, viruses, cadaveric tissue, archaeological/ancient samples, etc. In certain embodiments, the initial DNA used in the method may be derived from a mammal, where in certain embodiments the mammal is a human.

The method and kit described above finds use in a variety of applications, where such applications generally include sample analysis applications in which the presence of a target nucleic acid sequence in a given sample is detected. Because certain embodiments of the method are capable of producing a copy of a sequence in sample, the method finds particular use in targeted resequencing applications in which one or more loci within a genome are selected and then sequenced.

In particular, the above-described methods may be employed to diagnose a disease (e.g., an infectious disease, a neoplastic disease, e.g., cancer or an inflammatory disease), or to predict a response to treatment. Cancerous conditions of interest include but not limited to, leukemia, breast carcinoma, prostate cancer, Alzheimer's disease, Parkinson's disease, epilepsy, amyotrophic lateral sclerosis, multiple sclerosis, stroke, autism, mental retardation, and developmental disorders. Many nucleotide polymorphisms are associated with and are thought to be a factor in producing these disorders. Knowing the type and the location of the nucleotide polymorphism may greatly aid the diagnosis, prognosis, and understanding of various mammalian diseases. In addition, the assay conditions described herein can be employed in other nucleic acid detection applications including, for example, for the detection of infectious diseases, viral load monitoring, viral genotyping, environmental testing, food testing, forensics, epidemiology, and other areas where specific nucleic acid sequence detection is of use.

In some embodiments, a biological sample may be obtained from a patient, and the sample may be analyzed using the method. In particular embodiments, the method may be employed to identify and/or estimate the amount of mutant copies of a genomic locus that are in a biological sample that contains both wild type copies of a genomic locus and mutant copies of the genomic locus that have a point mutation relative to the wild type copies of the genomic locus.

In these embodiments, the method may be employed to detect an oncogenic mutation (which may be a somatic mutation) in, e.g., PIK3CA, NRAS, KRAS, JAK2, HRAS, FGFR3, FGFR1, EGFR, CDK4, BRAF, RET, PGDFRA, KIT or ERBB2, which mutation may be associated with breast cancer, melanoma, renal cancer, endometrial cancer, ovarian cancer, pancreatic cancer, leukemia, colorectal cancer, prostate cancer, mesothelioma, glioma, medulloblastoma, polycythemia, lymphoma, sarcoma or multiple myeloma (see, e.g., Chial 2008 Proto-oncogenes to oncogenes to cancer. Nature Education 1:1).

In one embodiment, a sample may be collected from a patient at a first location, e.g., in a clinical setting such as in a hospital or at a doctor's office, and the sample may be forwarded to a second location, e.g., a laboratory where it is processed and the above-described method is performed to generate a report. A "report" as described herein, is an electronic or tangible document which includes report elements that provide test results that may include a Ct value, or Cp value, or the like that indicates the presence of mutant copies of the genomic locus in the sample. Once generated, the report may be forwarded to another location (which may be the same location as the first location), where it may be interpreted by a health professional (e.g., a clinician, a laboratory technician, or a physician such as an oncologist, surgeon, pathologist), as part of a clinical diagnosis.

What is claimed is:

1. A method for sample analysis, comprising:
   a) enzymatically attaching a reactive group to nucleic acid molecules in a sample;
   b) covalently reacting said reactive group with reactive sites in a porous support, thereby covalently tethering said nucleic acid molecules to said porous support, wherein the porous support is a silica membrane;
   c) performing a primer extension reaction using said tethered nucleic acid molecules as a template to produce primer extension products, wherein the primer extension is done using one or more gene-specific primers that hybridize to a subset of the nucleic acid molecules that are tethered to the porous support but do not hybridize to an adaptor sequence; and
   d) eluting the primer extension products from the porous support, while leaving the tethered nucleic acid molecules tethered to said porous support, wherein said eluting is done by:
      (i) treating the product of step c) with heat or a chaotropic agent to denature the primer extension products from the tethered nucleic acid molecules; and
      (ii) applying a force that separates the primer extension products and the porous support.

2. The method of claim 1, wherein the enzymatically attaching adds an alkyne or azide group to the nucleic acid molecules.

3. The method of claim 1, wherein said enzymatically attaching comprises ligating an oligonucleotide comprising said reactive group to said nucleic acid molecules.

4. The method of claim 1, wherein the reactive sites on said porous support are alkyne or azide groups.

5. The method of claim 1, wherein the porous support is functionalized to contain reactive sites.

6. The method of claim 1, wherein the sample comprises genomic DNA that has been fragmented by physical, enzymatic or chemical treatment.

7. The method of claim 1, wherein the sample is obtained from a tissue biopsy.

8. The method of claim 1, wherein the sample is obtained from a patient having a condition or infectious disease.

9. The method of claim 1, wherein the force is a centrifugal force.

10. The method of claim 1, further comprising analyzing the eluted primer extension products.

11. The method of claim 10, wherein the analyzing comprises sequencing the eluted primer extension products.

12. The method of claim 1, further comprising, after step d), performing a second primer extension reaction using said tethered nucleic acid molecules as a template to produce second primer extension products.

13. The method of claim 1, wherein the sample comprises cDNA.

14. The method of claim 1, wherein the sample comprises RNA.

* * * * *